(12) United States Patent
Shin et al.

(10) Patent No.: US 6,303,356 B1
(45) Date of Patent: Oct. 16, 2001

(54) CELLULASE OR HEMICELLULASE MODIFIED BY CONJUGATION WITH A POLYETHYLENE GLYCOL FATTY ALCOHOL ETHER, AND A PROCESS FOR PRODUCING THE SAME

(75) Inventors: Jong-Ho Shin; Jeong Eun Kim; Steven Say-Kyoun Ow, all of Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 09/338,585

(22) Filed: Jun. 23, 1999

(30) Foreign Application Priority Data

Jun. 23, 1998 (KR) .................................. 98-23622

(51) Int. Cl.$^7$ ................ C12N 9/96; C12N 9/42
(52) U.S. Cl. .......................... 435/188; 435/209
(58) Field of Search ................ 435/177, 188, 435/209

(56) References Cited

PUBLICATIONS

Trends Biotechnol. 4, 190 (1986).
Biotechnol. Lett., 9, 187 (1987).
Biotechnol, Bioeng., 23, 1365 (1981).
Biotechnol. Bioeng., 28 1727 (1986).
J. Chem. Eng. Japan, 25 (2), 202 (1992).

*Primary Examiner*—Jon P. Weber
*Assistant Examiner*—Harry J Guttman

(57) ABSTRACT

The present invention relates to a modified enzyme and its modification process and more particularly, to the modified enzyme and its modification process, wherein amine group (—NH2) from amino acid residues of cellulose or hemicellulase, carbohydrase, is covalently coupled with the hydroxy and group (—OH) of polyoxyethylene fattyalcoholether expressed by the following formula 1 and then the modified enzyme exhibits a high stability of activities against pH and temperature as well as better enzyme activity.

$$RO-(CH_2CH_2O)_n-H \qquad (1)$$

Where, R is an alkyl group of 14 to 18 carbon atoms, and n is an integer of 3 to 12.

4 Claims, 1 Drawing Sheet

CELLULASE OR HEMICELLULASE MODIFIED BY CONJUGATION WITH A POLYETHYLENE GLYCOL FATTY ALCOHOL ETHER, AND A PROCESS FOR PRODUCING THE SAME

BACKGROUND OF THE INVENTION

1. Field of the Invention

The present invention relates to a modified enzyme and its modification process and more particularly, to the modified enzyme and its modification process, wherein amine group (—NH2) from amino acid residues of cellulase or hemicellulase, carbohydrase, is covalently coupled with the Polyethylene glycol fatty alcohol ether expressed by the following formula 1 and then the modified enzyme exhibits a high stability of activities against pH and temperature as well as better enzyme activity.

$$RO—(CH_2CH_2O)_n—H \quad (1)$$

Where, R is an alkyl group of 14 to 18 carbon atoms, and n is an integer of 3 to 12.

2. Description of the Related Art

Enzymes, biochemical molecules produced from fungi or bacteria, catalyze various reactions due to a high degree of specificity for their substrates. Now that excessive use of chemicals is mainly involved in more severe environmental contamination, many researches have focused on the utilization of environment-friendly enzymes.

For example, the use of enzyme for degradation of carbohydrate is advantageous in that reactions can be performed under very mild conditions, compared with the conventional acid hydrolysis, without any corrosion of devices and environmental problems. Nevertheless, the degradation method of enzyme is not easy for its actual application in an industrial field, since (1) the degradation rate by enzyme is slow, (2) enzymes lose their apparent activity during hydrolysis due to tight adsorption of enzymes to carbohydrate, (3) the compliance and stability of enzymes are poor against the outer environmental conditions (e.g., pH, temperature, foreign materials in an enzymatic system, etc.).

To overcome these shortcomings, the following conventional methods designed to immobilize enzymes have been reported: (1) coupling methods such as physical adsorption, ionic bonding, biochemical bonding or covalent bonding, (2) microencapsulated methods, (3) cross-linking methods by a cross-linking agent, and (4) combination methods thereof. Some literatures have disclosed a method of modifying some enzymes (e.g., catalase, lipase, peroxidase, and chymotrypsin) into a copolymer of polyethylene glycol and cyaruric chloride [Trends Biotechnol., 4, 190 (1986); Biotechnol. Lett. 9, 187 (1987)].

Up to now, studies on the chemical modification of cellulase and hemicellulase, carboyhdrase, have not been reported. The methods for treating cellulase have been mainly confined either to the enzymological studies designed to control the activity of each enzyme component via purification and separation of cellulase, or to researches designed to extract new enzymes from animals or plants.

In addition, some literatures have disclosed that the concurrent use of surfactant contributes much to enhancement of enzyme activity [Biotechnol. Bioeng., 23, 1365 (1981); Biotechnol. Bioeng., 28, 1727 (1986)]. A majority of recently commercialized enzymes contain the surfactant. However, a simple mixture containing enzyme and surfactant is highly sensitive to the outer environmental conditions (e.g., temperature, pH, etc.), thus restricting its wide use.

To enhance the stability of enzyme activity, some researchers have recently modified enzymes with a synthetic copolymer of polyethyleneglycol alkylallylether and maleic acid anhydride [J. Chem. Eng. Japan, 25(2), 202 (1992)]. The stability of enzyme activity has been modified to some extent but the nominal activity of modified enzyme is lower than that of unmodified native enzyme.

As described above, the conventional modification methods of enzyme, which are chiefly directed towards a simple mixing of enzyme with surfactants, are entirely different from the present invention. Further, the chemical modification of the present invention is significantly different from that of the above mentioned literatures [J. Chem. Eng. Japan, 25(2), 202(1992)] in terms of chemical structure of materials in use and performance of modified enzyme in improving the activity and stability.

SUMMARY OF THE INVENTION

Through intensive efforts to achieve an improvement in enzyme activity, the inventors have finally come to know that if a single substance comprising enzyme and surfactant is prepared via chemical coupling of enzyme and surfactant instead of a simple physical mixture of both enzyme and surfactant, the stability of enzyme activity can be significantly enhanced in a specific range of modification. Further, the inventors have noted that the significant activity of modified enzyme may be ensured by selecting polyoxyethylene fattyalcoholether (that is, a polyethylene glycol fatty alcohol ether) as a surfactant, which allows enzyme and substrate to be readily associated and dissociated. Thus, the inventors have completed the present invention.

Therefore, an object of the present invention is to provide a novel modified enzyme and the process for preparing such enzyme, wherein amine group (—NH2) from amino and residues of cellulase or hemicellulase, carbohydrase, is covalently coupled with the polyethylene glycol fatty alcohol either expressed by the following formula 1 and then the modified enzyme exhibits a high stability of activities against pH and temperature as well as better enzyme activity.

DETAILED DESCRIPTION OF THE INVENTION

Figure 1:
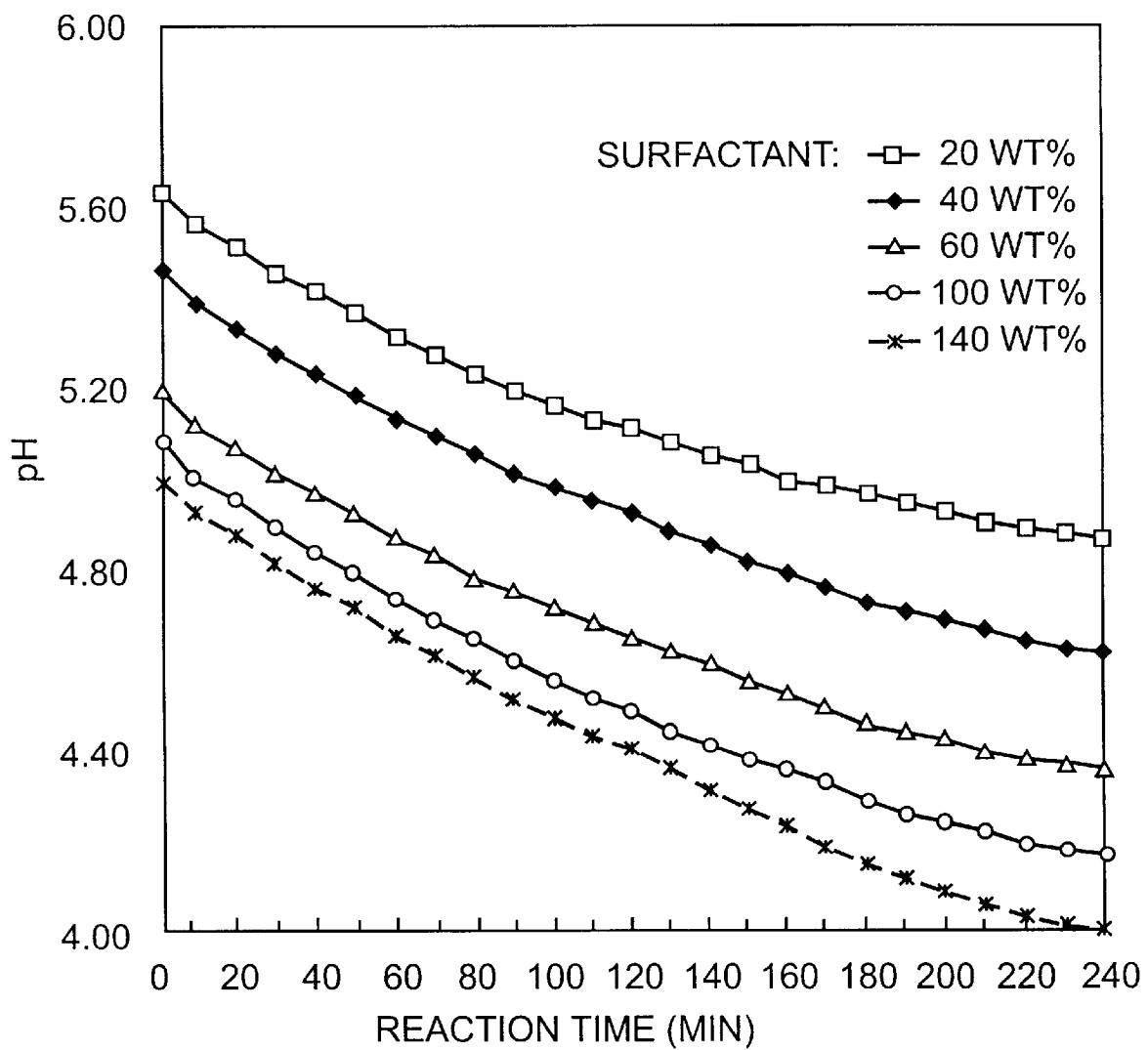
FIG. 1 shows the effect of reaction time on system pH.

The present invention is characterized by a novel modified enzyme comprising enzyme and surfactant, wherein a carbohydrase selected from cellulase or hemicellulase is covalently coupled with polyoxyethylene fattyalcoholether expressed by the following chemical formula 1:

$$RO—(CH_2CH_2O)_n—H \quad (1)$$

Where, R is an alkyl group of 14 of 18 carbon atoms, and n is an integer of 3 to 12.

Also, the present invention provides a process of manufacturing the modified enzyme, wherein polyoxyethlene fattyalcoholether is reacted with p-toluenesulfonyl chloride (p-TsCl) in the presence of pyridine to give p-tosylated polyoxyethylene fattyalcoholether and then a carbohydrase selected from cellulase or hemicellulase is covalently coupled with the above reactant.

The present invention is explained in more detail as set forth hereunder.

The present invention relates to a modified enzyme and its modification process. In this modification system, amine group (—NH2) of cellulase or hemicellulase is covalently coupled by trans-esterification with the specific nonionic surfactant and then the modified enzyme exhibits a high stability of activities against pH and temperature as well as better enzyme activity.

According to the present invention, cellulase is an enzyme that hydrolyzes cellulose, and hemicellulase (called cytase) is an enzyme that hydrolyzes hemicellulose. The activity of cellulase is represented by avicelase which serves to degrade a solid crystal of cellulose and CMCase which serves to degrade amorphous site of cellulose, while the activity of hemicellulase is represented by xylanase.

Generally, enzymes are polypeptides of amino acids, each joined to its neighbor by a specific type of covalent bonds. Amine groups in these amino acids are readily bound to hydroxyl groups of any substance via hydrolysis. However, since the reaction is performed in relatively severe conditions, enzyme loses their apparent activity during hydrolysis. To overcome such drawbacks, the present invention is characterized by obtaining a novel single substance comprising enzyme and surfactant, wherein the nonionic surfactant is reacted with p-toluenesulfonyl chloride to give p-tosylated polyoxyethylene fattyalcoholether and then the reactant is chemically coupled to the cellulase molecule under mild conditions of room temperature.

The modified enzyme of the present invention exhibits a high stability of activity at various pH conditions of 2~9 compared with the common optimum pH conditions of 3~6 in carbohydrase. Therefore, the novel enzyme of the present invention is advantageous in that its activity is maintained even under alkaline conditions, allowing the applicable pH conditions to be further enlarged, while the conventional carbohydrates exhibits limited activity in acidic conditions.

The following scheme 1 summarizes the process for preparing the modified enzyme of the present invention.

Scheme 1

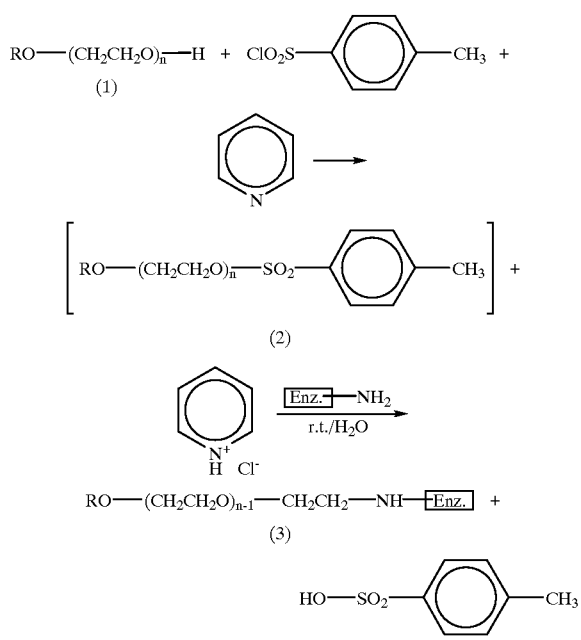

As shown in the scheme 1, an nonionic surfactant expressed by the formula 1 is reacted with p-toluenesulfonyl chloride (p-TsCl) in the presence of pyridine to give an intermediate of p-tosylated polyoxyethylene fattyalcohol-ether expressed by the formula 2. Then, selected enzyme is added to the given intermediate to modify the enzyme expressed by the formula 3 in such a manner that amine group (—NH2) of enzyme is covalently coupled by trans-esterification with the surfactant.

The salient aspect in the manufacture of the modified enzyme is that p-toluenesulfonyl group (p-tosyl group) is used as a good leaving group. Since the p-tosyl group is easily reacted with a nonionic surfactant expressed by the formula 1 to give the intermediate (chemical formula 2) with its easier dissociation under mild conditions of room temperature in reaction between the enzyme and intermediate, the p-tosyl group is suitable for the enzymatic reaction where enzyme activity may be changed depending on temperature-sensitive enzyme reaction.

20–100 weight parts of a nonionic surfactant expressed by the formula 1 is added to 100 parts weight of enzyme. If the amount of surfactant is less than 20 weight parts, stability of enzyme is slightly affected but in case of exceeding 100 weight parts, the enzyme activity is decreased and thus a more high production cost is inevitable.

As described above, the modified enzyme exhibits a high stability of activities against pH and temperature as well as better enzyme activity.

The following example illustrate various aspects of this invention but are not to be construed to limit the claims in any manner whatsoever.

Example

Preparation of modified enzyme

A mixture containing 272 g of nonionic surfactant expressed by RO(CH$_2$CH$_2$O)$_n$H (R=alkyl group of 14 to 18 carbon atoms, n=10), 143 g of p-toluenesulfonyl chloride and 60 g of pyridine was added to 400 ml of methylene chloride. The reaction mixture was refluxed for 2~6 hours, cooled to room temperature, and allowed to stand for 4 hours. Then, the precipitated needle-like crystal of pyridine chloride was filtered off. The reaction mixture was washed successively with diluted 0.1N HCl solution (100 ml) to remove residual pyridine and with water three times. After the solvent was evaporated to obtain P-tosylated polyoxyethylene fattyalcoholether (yield: 92%). The formation of pyridinium chloride verified chemically the production of the compound expressed by the formula 2.

100 g of cellulase [Penicillium funiculsosum (EC 3,2,1,4): Sigma Chemical Co., USA] was added to 100 g of p-tosylated polyethylene fattyalcoholether in water, so formed, and stirred at room temperature for 4 hours to obtain the modified enzyme.

To follow up the modification process, the attached FIG. 1 showed the effect of reaction time on system pH.

According to the scheme 1, the enzyme was coupled with p-tosylated polyoxyethylene fattyalcoholether and then p-toluene sulfonic acid was produced as a reaction by-product. Thus, it was noted that as the reaction proceeded, pH was decreased gradually.

Experimental example

To compare the activity of the modified enzyme, so prepared from the present invention, with the enzyme from a simple mixing of enzyme and surfactant, activity of cellulase was determined by relative avicelase and relative CMCase, respectively, from absorbance at 575 nm by UV spectrophotometer based on the dinitrosalicilic acid (DNS) method. Activity of hemicellulase was determined by relative xylanase based on the DNS method. Hence, the relative activities were defined by the relative increase or decrease rate of enzyme activity in a simple mixture of enzyme and surfactant (hereinafter referred to as "mixed enzyme") and the modified enzyme by surfactant (hereinafter referred to as "modified enzyme"), when the activity of native enzyme (hereinafter referred to as "unmodified enzyme") was calculated as 1.0.

Experimental Example 1

Determination of activities based on the amount of nonionic surfactant

The modified enzyme was prepared in the same manner as Example, except that each different amount of nonionic surfactant expressed by $RO(CH_2CH_2O)_nH$ (R=an alkyl group of 14 to 18 carbon atom, n=10) was used in proportion to 100 parts by weight, as shown in table 1.

TABLE 1

Comparison of relative activities based on the amount of nonionic surfactant in proportion to 100 parts by weight

| | cellulase | | | | hemicelluase | |
|---|---|---|---|---|---|---|
| | avicelase | | CMCase | | xylanase | |
| Section | Modified enzyme | Mixed enxyme | Modified enzyme | Mixed enxyme | Modified enzyme | Mixed enxyme |
| surfactant | | | | | | |
| 20 | 1.06 | 0.68 | 0.99 | 0.59 | 1.17 | 0.72 |
| 40 | 1.12 | 0.75 | 1.07 | 0.61 | 1.24 | 0.84 |
| 60 | 1.18 | 0.88 | 1.18 | 0.64 | 1.29 | 0.90 |
| 80 | 1.25 | 1.07 | 1.29 | 0.98 | 1.33 | 1.13 |
| 100 | 1.23 | 1.10 | 1.18 | 1.02 | 1.35 | 1.22 |
| 140 | 0.89 | 1.22 | 1.09 | 1.09 | 0.9i | 1.32 |
| 160 | 0.88 | 1.20 | 1.04 | 1.30 | 0.87 | 1.30 |
| 180 | — | 1.21 | 1.02 | 1.33 | 0.88 | 1.32 |
| 200 | — | 1.20 | 1.01 | 1.33 | 0.89 | 1.31 |

1) celluase [*Penicillium funiculosum* (EC 3.2.1.4); U.S.A. Sigma]
2) hemicelluase [*Aspergillus niger* (EC 3.2.1.4); U.S.A. Sigma]

As the weight ratio of surfactant to enzyme was increased, the relative activity of modified enzyme was increased up to a maximum 30% compared with unmodified native enzyme. The relative activity of modified enzyme was superior to that of mixed enzyme. As the amount of surfactant to enzyme exceed 100 weight parts, however, activities of both avicelase and CMCase were decreased; in particular, avicelase activity showed more drastically decrease. Similar results were obtained in xylanase activity to hemicellulase. From the above table 1, it was noted that the surfactant used for the present invention could modify the enzyme with increased activity but excessive use of surfactant resulted in the decrease of enzyme activity due to change in physical structure of enzyme. As the amount of surfactant to enzyme exceed 100 parts by weight, the activity of mixed enzyme was increased in a similar manner to that of modified enzyme, while requiring more surfactants than modified enzyme.

Experimental Example 2

Determination of activity based on polymerization degree of ethyleneoxide in nonionic surfactant To determine the activity of modified enzyme based on the polymerization degree of ethyleneoxide in surfactant, the modified enzyme was prepared in the same manner as Example, except that 80 weight parts of nonionic surfactant expressed by $RO(CH_2CH_2O)_nH$ (R=alkyl group of 14 to 18 carbon atom, n=10) was used in proportion to 100 weight parts, as shown in table 2.

TABLE 2

Comparison of relative activities based on the unit number of ethleneoxide (EO) repeating unit in nonionic surfactant

| | cellulase | | | | hemicelluase | |
|---|---|---|---|---|---|---|
| | avicelase | | CMCase | | xylanase | |
| Section | Modified enzyme | Mixed enxyme | Modified enzyme | Mixed enxyme | Modified enzyme | Mixed enxyme |
| Surfactant (unit) | | | | | | |
| 3 | 1.02 | 0.62 | 1.00 | 0.57 | 1.10 | 0.73 |
| 5 | 1.10 | 0.73 | 1.04 | 0.68 | 1.21 | 0.82 |
| 7 | 1.18 | 0.89 | 1.13 | 0.86 | 1.29 | 0.97 |
| 10 | 1.25 | 1.04 | 1.29 | 1.04 | 1.32 | 1.15 |
| 12 | 1.08 | 1.20 | 1.12 | 1.27 | 1.18 | 1.31 |
| 15 | 0.78 | 1.18 | 0.70 | 1.31 | 0.86 | 1.29 |

1) celluase [*Penicillium funiculosum* (EC 3.2.1.4); U.S.A. Sigma]
2) hemicelluase [*Aspergillus niger* (EC 3.2.1.4); U.S.A. Sigma]

In the above table 2, it was revealed that as the unit number of EO was increased, relative avicelase activity was nearly increased in straight line, showing the increased activity of up to 20% when the unit number of EO was 10. However, as the unit number of EO exceeded 10, relative avicelase activity was decreased. As the unit number of EO exceeded 12, markedly decreased activity was observed compared with native enzyme. Since surfactant with a large unit number of EO was more hydrophilic, the modified enzyme was less hydrophobic when the unit number of EO increased. According to the present invention, therefore, the hydrophobic and hydrophilic balance of surfactant is one of the important parameters in the enzymatic system.

Experimental Example 3

Effect of pH on relative activities of avicelase and CMCase

The modified enzyme was prepared in the same manner as Example, except the 80 weight parts of nonionic surfactant expressed by $RO—(CH_2CH_2O)_n—H$ (R=an alkyl group of 14 to 18 carbon atom, n=10) was used in proportion to 100 weight parts. Each dispersion solution of modified enzyme and mixed enzyme was allowed to stand at 50° C. for 20 hours at different pH conditions of 2~10 (pH 2, 3, 4, 5, 6, 7, 8, 9 and 10). Then, each activity of modified enzyme and mixed enzyme against temperature and pH was measured, as shown in table 3.

TABLE 3

| | cellulase | | | | hemicelluase | |
|---|---|---|---|---|---|---|
| | avicelase | | CMCase | | xylanase | |
| Section | Modified enzyme | Mixed enxyme | Modified enzyme | Mixed enxyme | Modified enzyme | Mixed enxyme |
| surfactant | | | | | | |
| 2 | 0.53 | 0.41 | 0.72 | 0.60 | 0.62 | 0.49 |
| 3 | 0.63 | 0.50 | 0.73 | 0.63 | 0.74 | 0.60 |

TABLE 3-continued

| | cellulase | | | | hemicelluase | |
|---|---|---|---|---|---|---|
| | avicelase | | CMCase | | xylanase | |
| Section | Modified enzyme | Mixed enxyme | Modified enzyme | Mixed enxyme | Modified enzyme | Mixed enxyme |
| 4 | 0.65 | 0.55 | 0.74 | 0.67 | 0.79 | 0.66 |
| 5 | 0.61 | 0.55 | 0.79 | 0.69 | 0.75 | 0.67 |
| 6 | 0.62 | 0.53 | 0.81 | 0.65 | 0.75 | 0.64 |
| 7 | 0.61 | 0.48 | 0.80 | 0.59 | 0.73 | 0.60 |
| 8 | 0.60 | 0.45 | 0.79 | 0.56 | 0.71 | 0.57 |
| 9 | 0.59 | 0.40 | 0.82 | 0.53 | 0.72 | 0.53 |
| 10 | 0.31 | 0.23 | 0.49 | 0.90 | 0.44 | 0.35 |

1) celluase [*Penicillium funiculosum* (EC 3.2.1.4); U.S.A. Sigma]
2) hemicelluase [*Aspergillus niger* (EC 3.2.1.4); U.S.A. Sigma]

In the above table 3, activity of mixed enzyme containing a simply mixture of enzyme and surfactant was increased at pH 3.0~6.0 but decreased significantly at alkaline pH conditions of more than 7.0. Meanwhile, the stable activity of the modified enzyme, determined by avicelase and CMCase, was relatively enlarged to pH 2.0~9.0.

As described the above, the modified enzyme of the present invention by the modification of nonionic surfactant shows a high activity of activities. Especially, when 80~100 weight parts of surfactant is used to 100 weight parts of carbohydrase, relative activities of avicelase, CMCase and xylanase are increased by 25~30%. In general, the modified enzyme shows a high stability of activities in that the using range of carbohydrase, which is usually deactivated at alkaline pH conditions, can be enlarged to pH 2.0~9.0 at the applicable temperature of 50° C.

What is claimed is:

1. A surfactant modified carbohydrase enzyme, wherein a carbohydrase enzyme selected from cellulase and hemicellulase is covalently coupled with a polyethylene glycol fatty alcohol ether of formula (1) below:

$$RO-(CH_2CH_2O)_n-H \quad (1),$$

to produce the surfactant modified carbohydrase enzyme of formula (3) below:

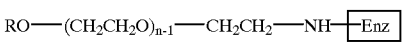 (3)

wherein R is an alkyl group comprising from 14 to 18 carbon atoms, and n is an integer ranging from 3 to 12.

2. The surfactant modified carbohydrase enzyme according to claim 1, wherein said surfactant modified carbohydrase enzyme has a high stability of activity in the range of pH 2.0~9.0.

3. A process for preparing a surfactant modified carbohydrase enzyme expressed by formula (3) below, comprising reacting a non-ionic surfactant chosen from polethylene glycol fatty alcohol ethers of formula (1) below with p-toluene sulfonyl chloride in the presence of pyridine to yield p-tosylated polyethylene fattyalcoholether of formula (2) below; and reacting said p-tosylated polyethylene fattyalcoholether of formula (2) with a carbohydrase enzyme selected from cellulase and hemicellulase to prepare the surfactant modified carbohydrase enzyme;

$$RO-(CH_2CH_2O)_n-H \quad (1)$$

 (2)

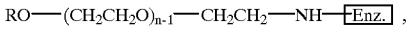 , (3)

wherein R is an alkyl group comprising from 14 to 18 carbon atoms, and n is an integer ranging from 3 to 12.

4. The process according to claim 3, wherein said nonionic surfactant is added, in an amount ranging from approximately 20 to approximately 100 parts by weight, to 100 parts by weight of said carbohydrase enzyme.

* * * * *

UNITED STATES PATENT AND TRADEMARK OFFICE
CERTIFICATE OF CORRECTION

PATENT NO.    : 6,303,356 B1                                    Page 1 of 1
DATED         : October 16, 2001
INVENTOR(S)   : Jong Ho Shin et al.

It is certified that error appears in the above-identified patent and that said Letters Patent is hereby corrected as shown below:

<u>Title page,</u>
ABSTRACT, line 4, change "cellulose" to -- cellulase --;
Line 6, change "and group" to -- end group --.

Signed and Sealed this

Fifth Day of March, 2002

*Attest:*

*Attesting Officer*

JAMES E. ROGAN
*Director of the United States Patent and Trademark Office*